United States Patent
Rocha Ferreira (10) Patent No.: US 11,957,539 B2
(45) Date of Patent: Apr. 16, 2024

(54) DENTAL PROSTHESIS SYSTEM, FOR THE USE WITH AT LEAST TWO DENTAL IMPLANTS

(71) Applicant: UNIVERSIDADE DO PORTO, Oporto (PT)

(72) Inventor: Jose Joaquim Rocha Ferreira, Oporto (PT)

(73) Assignee: UNIVERSIDADE DO PORTO, Oporto (PT)

( * ) Notice: Subject to any disclaimer, the term of this patent is extended or adjusted under 35 U.S.C. 154(b) by 332 days.

(21) Appl. No.: 17/272,140

(22) PCT Filed: Aug. 27, 2019

(86) PCT No.: PCT/PT2019/050030
§ 371 (c)(1),
(2) Date: Feb. 26, 2021

(87) PCT Pub. No.: WO2020/046154
PCT Pub. Date: Mar. 5, 2020

(65) Prior Publication Data
US 2021/0338386 A1 Nov. 4, 2021

(30) Foreign Application Priority Data
Aug. 29, 2018 (PT) .......................................... 111117

(51) Int. Cl.
*A61C 8/00* (2006.01)
*A61K 6/836* (2020.01)
*A61K 6/849* (2020.01)

(52) U.S. Cl.
CPC .......... *A61C 8/0068* (2013.01); *A61C 8/0016* (2013.01); *A61C 8/0027* (2013.01);
(Continued)

(58) Field of Classification Search
CPC ... A61C 8/0068; A61C 8/0016; A61C 8/0027; A61C 8/0078; A61C 8/0042; A61C 8/0043; A61K 6/849; A61K 6/836
See application file for complete search history.

(56) References Cited

U.S. PATENT DOCUMENTS 3,955,280 A * 5/1976 Sneer .................... A61C 8/0069
433/169
4,682,951 A * 7/1987 Linkow ................ A61C 8/0092
433/176

(Continued)

OTHER PUBLICATIONS

International Search Report and Written Opinion for corresponding International Application No. PCT/PT2019/050030 dated Dec. 9, 2019; 9 pages.

*Primary Examiner* — Nicholas D Lucchesi
*Assistant Examiner* — Hao D Mai
(74) *Attorney, Agent, or Firm* — Lucas & Mercanti, LLP (57) ABSTRACT

A dental prosthesis system, for the use with at least two dental implants, wherein the dental prosthesis is divided in a first prosthetic part and a second prosthetic part, jointed by a prosthetic screw, and wherein the first prosthetic part is connected to the dental implants through at least two connectors, and such dental prosthesis has an engaging and guidance system, including two female elements, disposed on the top of the first prosthetic part, and two corresponding male elements, disposed on the bottom of the second prosthetic part, whereby the connection between the two female elements and the two male elements is releasable.

16 Claims, 6 Drawing Sheets

(52) U.S. Cl.
CPC ............ *A61C 8/0078* (2013.01); *A61K 6/836* (2020.01); *A61K 6/849* (2020.01)

(56) References Cited

U.S. PATENT DOCUMENTS

| | | | | |
|---|---|---|---|---|
| 5,221,205 | A * | 6/1993 | Kuch | A61C 13/26 433/181 |
| 5,564,925 | A * | 10/1996 | Shampanier | A61C 8/0018 433/173 |
| 7,806,685 | B1 * | 10/2010 | Grant | A61C 8/005 433/14 |
| 8,287,278 | B2 * | 10/2012 | Grant | A61C 8/0069 433/174 |
| 8,449,297 | B2 * | 5/2013 | Boehm-Van Diggelen | A61C 8/0019 433/173 |
| 9,522,053 | B2 * | 12/2016 | Vukas | A61C 8/005 |
| 9,737,376 | B2 * | 8/2017 | Stewart | A61C 8/0089 |
| 2002/0192620 | A1 | 12/2002 | Jorneus et al. | |
| 2003/0064349 | A1 | 4/2003 | Simmons, Jr. | |
| 2003/0232308 | A1 * | 12/2003 | Simmons, Jr. | A61C 8/0031 433/173 |
| 2005/0084822 | A1 * | 4/2005 | Stucki-McCormick | A61C 8/0018 433/173 |
| 2007/0072150 | A1 * | 3/2007 | Mansueto | A61C 8/0066 433/174 |
| 2008/0118885 | A1 * | 5/2008 | Devincenzo | A61C 7/00 433/10 |
| 2008/0153060 | A1 * | 6/2008 | De Moyer | A61C 1/084 433/201.1 |
| 2008/0171307 | A1 * | 7/2008 | Wilcox | A61C 8/0048 433/222.1 |
| 2008/0293012 | A1 * | 11/2008 | Chaves | A61C 8/0077 433/173 |
| 2009/0171396 | A1 * | 7/2009 | Baynham | A61B 17/8038 606/301 |
| 2009/0258329 | A1 * | 10/2009 | Adams | A61C 8/0043 433/174 |
| 2010/0003635 | A1 * | 1/2010 | Feith | A61C 8/0018 433/201.1 |
| 2010/0248189 | A1 * | 9/2010 | Burger | A61C 5/20 427/2.29 |
| 2010/0291507 | A1 * | 11/2010 | Abdelgany | A61C 8/0053 433/174 |
| 2011/0027756 | A1 * | 2/2011 | Benatouil | A61C 8/0034 433/174 |
| 2011/0151408 | A1 * | 6/2011 | Grant | A61C 8/0022 433/174 |
| 2012/0122057 | A1 | 5/2012 | Adams | |
| 2013/0309632 | A1 * | 11/2013 | Sanders | A61C 8/0053 433/173 |
| 2014/0127642 | A1 * | 5/2014 | Lee | A61C 13/26 433/172 |
| 2015/0111174 | A1 | 4/2015 | Katto | |
| 2016/0278887 | A1 * | 9/2016 | Hornbeck | A61C 8/0068 |
| 2017/0189147 | A1 * | 7/2017 | Cho | A61C 13/087 |
| 2017/0202649 | A1 * | 7/2017 | Bernhard | A61C 8/0066 |
| 2017/0239020 | A1 * | 8/2017 | McDonald | A61C 8/0039 |
| 2017/0360536 | A1 * | 12/2017 | Alqarawi | A61C 13/0018 |
| 2018/0028284 | A1 * | 2/2018 | Thomke | A61C 8/0043 |
| 2018/0280121 | A1 * | 10/2018 | Zhang | A61C 13/2255 |
| 2021/0338386 | A1 * | 11/2021 | Rocha Ferreira | A61C 8/0068 |

* cited by examiner

DENTAL PROSTHESIS SYSTEM, FOR THE USE WITH AT LEAST TWO DENTAL IMPLANTS

CROSS-REFERENCE TO RELATED APPLICATIONS

This application is a 371 of PCT/PT2019/050030, filed Aug. 27, 2019, which claims the benefit of Portuguese Patent Application No. 111117, filed Aug. 29, 2018, each of which are incorporated herein by reference.

FIELD OF THE INVENTION

The present invention is related to a dental prosthesis system, for the use with at least two dental implants, which is suited to be used in oral rehabilitations.

STATE OF THE ART

Oral rehabilitations using osseointegrated implants have proven to be an effective solution, with evidence of good long-term results and which gives back the patient the lost masticatory and aesthetic functions, as it is shown in Adell et al. ("A 15-year study of osseointegrated implants in the treatment of the edentulous jaw." Int J Oral Surg. 1981; 10(6):387-416), in Jemt T, Johansson J. ("Implant treatment in the edentulous maxillae: A 15-year followup study on 76 consecutive patients provided with fixed prostheses." Clin Implant Dent Relat Res. 2006; 8(2):61-9) and in Lindquist et al. ("A prospective 15-year follow-up study of mandibular fixed prostheses supported by osseointegrated implants." Clinical results and marginal bone loss. Clin Oral Implants Res. 1996; 7(4):329-36). However, due to different causes, the available bone volume may difficult the placement of dental implants, either because the prosthetically driven placement of the fixations may be compromised or because the use of implants of conventional dimensions is prevented by the proximity of important anatomical structures.

Thus, in order to overcome this problem, the use of surgical procedures to re-establish the bone volume and contour for a prosthetically driven implant insertion as well as for the placement of conventionally dimensioned implants, appears as an attractive option. The different surgical approaches comprehend a vast group of bone grafts (autografts, allografts, xenografts and synthetic bone grafts) and techniques, with multiple combinations (onlay bone grafts, interpositional bone grafts, guided bone regeneration, distraction osteogenesis and split crest). However, despite the success rates reported, these procedures are related with expensive treatments, more surgeries, more morbidity, more surgical complications, more treatment time and the increasing of the possibility of failure. These factors prompt the patient and the dentist to seek for simpler, faster and cheaper solutions.

As an alternative, the use of short implants, placed on the available bone, is cheaper, quicker and less invasive. This group of implants is particularly indicated when the amount of bone is reduced. Furthermore, the use of short implants makes unnecessary more complex surgical approaches. Nevertheless, this solution may also present some drawbacks regarding the compromised crown-to-implant ratio and the prosthetic outcome. Whenever it is necessary, the recourse to prosthetic solutions to correct the prosthetically unfavourable implant positioning may be a helping and complementary approach.

Another option to overcome the implant placement in a not prosthetically oriented way, is the recourse to cemented prosthesis. The cemented restorations have some advantages as a better aesthetic outcome due to the absence of the screw access and the simplicity of use. However, they are also related with problems concerning the prosthesis retrievability, sometimes requiring the prosthesis perforation to find the abutment screw, which may result in a significant aesthetic damage and the need to replace the prosthesis, as it is shown in Mehl et al. ("Retrievability of implant-retained crowns following cementation." Clin Oral Implants Res. 2008; 19(12):1304-11). Nevertheless, the major problem identified with the use of cemented prosthesis is the difficult excess of cement removal and the possibility of developing peri-implant problems, ranged from a peri-implant inflammation associated with swelling, bleeding and deeper probing, besides signs of bone loss, as it is shown in Pauletto et al. ("Complications associated with excess cement around crowns on osseointegrated implants: a clinical report." Int J Oral Maxillofac Implants. 1999; 14(6):865-8). The use of angled abutments may also be considered as a possible approach on such cases which may allow for the use of a screw retained solution. The use of angulated screw channels, also known as dynamic abutments, is also a solution for the same clinical problems, as it is stated in Ferreira et al. ("Fatigue and microgap behaviour of a three-unit implant-fixed dental prosthesis combining conventional and dynamic abutments". J Med Eng Technol. 2018; 42(5): 397-405).

A common and paramount problem regarding an implant placement, without previous bone augmentation procedures, is related to the bending forces generated on the prosthetic components, implants and bone by a clinical prostheses considerably higher than the supporting implants and the possible adverse effects on the bone tissue and on the implants and prosthetic components, as it is shown in Calvo et al. ("Evaluation of extrashort 4-mm implants in mandibular edentulous patients with reduced bone height in comparison with standard implants: a 12-month results." Clin Oral Implants Res. 2015; 27:867-74) and in Verri et al. ("Biomechanical influence of crown-to-implant ratio on stress distribution over internal hexagon short implant: 3-D finite element analysis with statistical test." J Biomech. 2015; 48(1):138-45). Likewise, the effect of the bending moments produced by the masticatory forces are also motive of concern once the bone's yield strength is lower when the load is acting on a perpendicular direction to its major axis.

Therefore, despite the documented safety of use, the short implants may be related with an increased risk of implant failure.

The rationale behind this issue is supported by the fact that the masticatory forces, due to their horizontal component, create a bending moment that could generate high compressive and shear stresses on the marginal bone. As the use of short implants may be related with the need for long crowns, creating a bigger crown-to-implant ratio, it can be assumed that the greater the crown, the greater the bending moment and, as consequence, also the greater is the possibility of higher stresses, with potential detrimental effects, being generated at the marginal bone level. The fulcrum for the rotation resultant of the considered moment could be placed at the implant-abutment interface, usually at the bone crest level.

Therefore, there is a necessity in the state of the art concerning about the development of long-term aesthetic and functional treatments, wherein "long-term" means biomechanical stability of hard and soft tissues and also stability of the materials used to replace the lost tissues and the lost teeth. Moreover, there is a necessity of developing a dental prosthesis system wherein its main structural components may be able to resist to the stresses generated by bending moments, resultant for the masticatory forces, whereas it is preserved the bone tissues supporting the implant and the prosthesis.

BRIEF DESCRIPTION OF THE DRAWINGS

In order to promote an understanding of the principles according to the embodiments of the present invention, reference will be made to the embodiments shown in the figures and to the language used to describe them. In any event, it is to be understood that there is no intention to limit the scope of the present invention to the contents of the figures. Any subsequent changes or modifications of the inventive features herein and any further applications of the principles and embodiments of the invention illustrated which would normally occur to a person skilled in the art having the possession of this disclosure are within the scope of the claimed invention.

LIST OF REFERENCE NUMBERS a first prosthetic part (1);
a second prosthetic part (2);
a prosthetic screw (3);
a connector (4);
a male element (5);
a female element (6);
a projection as male element (5a);
a groove as female element (6a);
a conical or cylindrical extension as male element (5b);
a conical or cylindrical cavity as female element (6b);
a prosthetic screw channel (7);
a model of a cortical bone (8);
a model of a trabecular bone (9);
a implant screw channel (10);
a buccal face (11); and
a lingual face (12).

DETAILED DESCRIPTION OF THE PREFERRED EMBODIMENTS

Reference will now be made in detail to the preferred embodiments of the invention, examples of which are illustrated in the accompanying drawings. Whenever possible, the same reference numerals will be used throughout the drawings to refer to the same or like parts.

Having the problems of the state of the art in mind, the present invention is based on installing a mechanical weakness in the prosthesis to protect the bone tissue from the bending moment resultant from the masticatory forces. The present invention explores the concept of a mechanical or structural fuse, which comprises the introduction of a sacrificial element that, in case of overload and/or fatigue, will break or deform and, therefore, protect the remaining structure. The transposition of this engineering concept to a clinical situation would result in the fracture or the necking of the sacrificial element avoiding the generation of a stress pattern that could result in marginal bone loss.

At the same time, the sacrificial element must be strong enough to resist to the normal masticatory function without failing and without allowing prosthetic movements that could make mastication uncomfortable. Furthermore, the programmed substitution of the sacrificial element is a cost-effective solution and is a solution that may be fully accepted by the patients.

The present invention refers to a dental prosthesis system, for the use with at least two dental implants, comprising:
the dental prosthesis, which is divided in two parts comprises a first prosthetic part (1), with a mesial, distal, lingual and buccal faces, a top section and a bottom section, and a second prosthetic part (2), with a mesial, distal, lingual and buccal faces, a top section and a bottom section; and
having a prosthetic screw (3), wherein the prosthetic screw joints the first prosthetic part (1) and the second prosthetic part (2), and said prosthetic screw (3) acts as a sacrificial element; and
wherein the first prosthetic part (1) is capable of being connected to the dental implants through at least two connectors (4), arranged in the bottom section of the first prosthetic part (1); and
having an engaging and guidance system, wherein the engaging and guiding system includes two female elements (6), disposed on the top section of the first prosthetic part (1), and two corresponding male elements (5), disposed on the bottom section of the second prosthetic part (2), whereby the connection between the two female elements (6) and the two male elements (5) is releasable.

The prosthetic screw (3) constitutes the sacrificial element subjected to a bending moment resultant from the masticatory forces acting upon the dental prosthesis system, implants and the bone tissue. The dental prosthesis system according to the present invention allows that the bone stress is placed in a safe zone. According to Frost's mechanostat theory, above a stress of 60 MPa upon the bone, microdamages can begin to accumulate unrepaired and the woven bone formation begins to replace the lamellar bone formation. Therefore, this point is the equivalent to the yield strength of the bone tissue. In the dental prosthesis system model according to the present invention, this bone remodelling does not happen, because the stresses upon the bone are maintained lower than the yield strength of the bone tissue, whereas the prosthetic screw (3) is submitted to a stress above its yield strength.

Therefore, after a certain period, wherein the dental prosthesis system is submitted to the shearing stresses resultant from the normal masticatory function, the mechanical weakness created by its division into a first prosthetic part (1) and a second prosthetic part (2), assembled by a prosthetic screw (3), acts protecting the bone tissue from the generation of stresses related with woven bone formation. Therefore, the prosthetic screw (3) is submitted to a stress above its elastic limit, as the other parts of the dental prosthesis system and the bone are submitted to stresses below its elastic limits. Ultimately, the prosthetic screw (3) fractures or deforms, keeping preserved the bone tissue and the prosthetic parts. If the prosthetic screw (3) breaks or deforms, this sacrificial element can be replaced and the dental prosthesis system is reinstalled over the implants, resulting in a cost-effective solution to the patient and a practical solution for the dentist.

The prosthetic screw may also be preventively replaced periodically.

Figure 1:
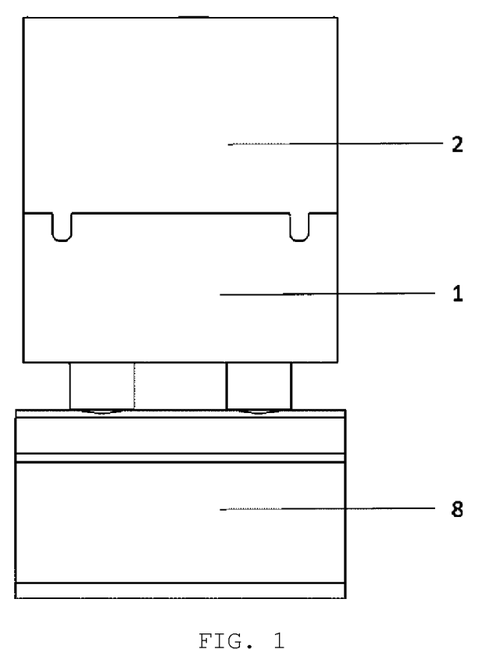
FIG. 1—is a frontal view of a dental prosthesis system, according to the present invention, connected to a model of a cortical bone.

As it is illustrated in FIG. 1, in a preferred embodiment of the present invention, it is performed a horizontal division of the dental prosthesis into a first prosthetic part (1) and a second prosthetic part (2), wherein the height of the second prosthetic part (2) is in a range from 20% to 80% of the existent crown height space. Preferably, the height of the second prosthetic part (2) is in, at least, 50% of the existent crown height space. The crown height space herein corresponds to the sum of the first prosthetic part (1) and second prosthetic part (2) heights.

In the preferred embodiments according to the present invention, the crown height space is equal or superior to 5 mm. According to Nissan et al. ("The effect of splinting implant-supported restorations on stress distribution of different crown-implant ratios and crown height spaces." J Oral Maxillofac Surg. 2011; 69(12):2990-4, there is a greater importance of the crown height space than the crown-to-implant ratio on the stress generation, mainly on the crestal bone level. According to this study, the crown-to-implant ratio does not seem to be responsible for the problems reported with the use of short implants. Instead, the crown height space plays a more relevant role, wherein from a 15 mm crown height on, the effects of marginal bone loss may start. Accordingly, in the tests employing a first prosthetic part (1) and second prosthetic part (2) resulting in crown height over 15 mm, the prosthetic screw (3) acts as a sacrificial element, subjected to a bending moment resultant from the masticatory forces, preserving the bone tissue.

Therefore, the dental prosthesis system according to the present invention can be used in a broad range of crown height spaces. Preferably, when the crown height space is equal or superior to 15 mm but may be used, whenever the crown height space is higher than the anatomical crown to be replaced.

The division of the prosthesis in a first prosthetic part (1) and a second prosthetic part (2) has introduced in the dental prosthesis system according to present invention a discontinuity in such a way that the dental prosthesis system does not behave as a rigid body. Analysing the stress pattern, the contacts and the displacements in both prosthetic parts, it is possible to describe their mechanical behaviour during the load appliance. The second prosthetic part suffers a rotation which is discontinued in the transition from the first prosthetic part (1) to the second prosthetic part (2). According to the model validation of the present invention, the second prosthetic part suffers a greater rotation than the first prosthetic part. Observing the stress generated on the buccal edge and the displacements of the second prosthetic part and the first prosthetic part, it may be stated that the centre of the rotation of the second prosthetic part is the edge along the first prosthetic part on the buccal face. Because this rotation is not counteracted by any structure, the groove engaging system also allows a small sliding of the second prosthetic part (2) over the first prosthetic part (1).

Figure 2:
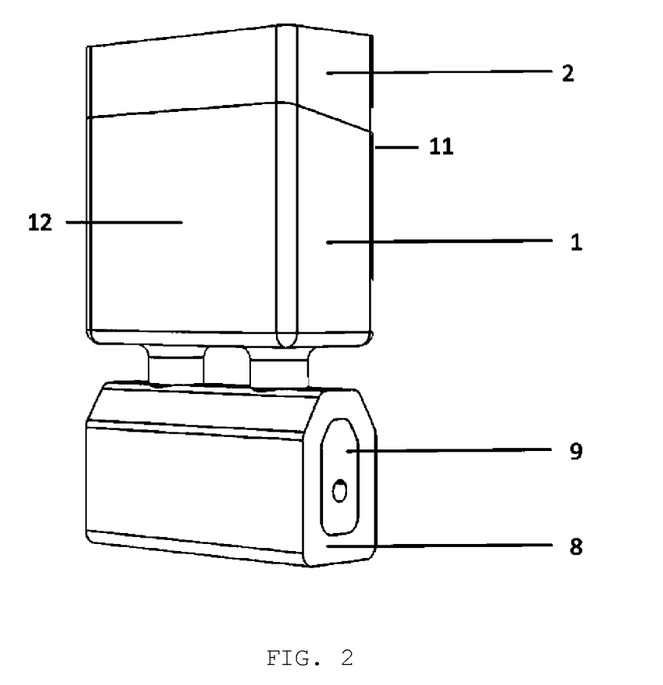
FIG. 2—is a frontal and a side view of a dental prosthesis system, according to the present invention, connected to a model of a cortical bone and trabecular bone.
Figure 3:
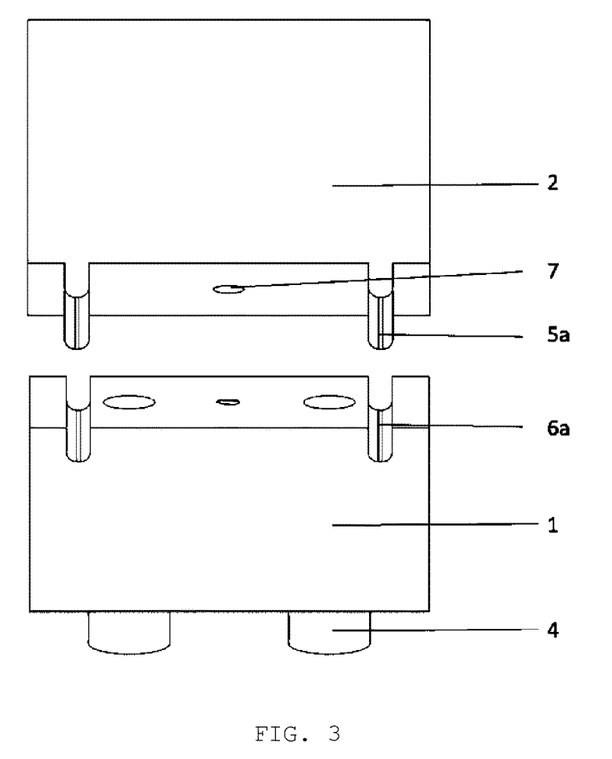
FIG. 3—is a view of a projection male element and a groove female element, used in an embodiment of the dental prosthesis system.
Figure 4:
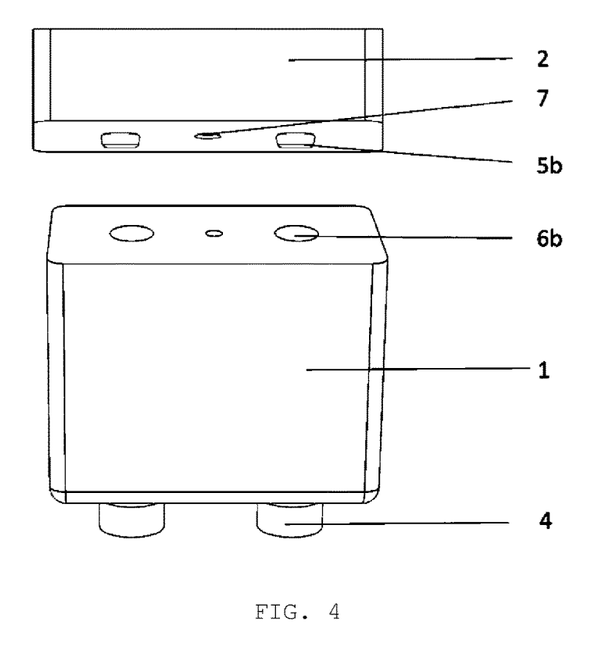
FIG. 4—is a view of a conical male element and a conical female element, used in an embodiment of the dental prosthesis system.
Figure 5:
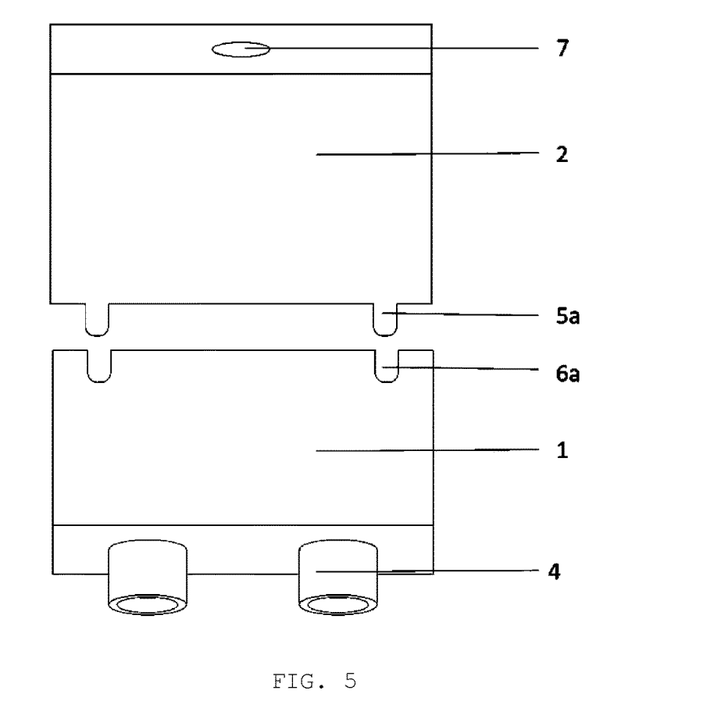
FIG. 5—is another view of a projection male element and a groove female element, used in an embodiment of the dental prosthesis system.
Figure 6:
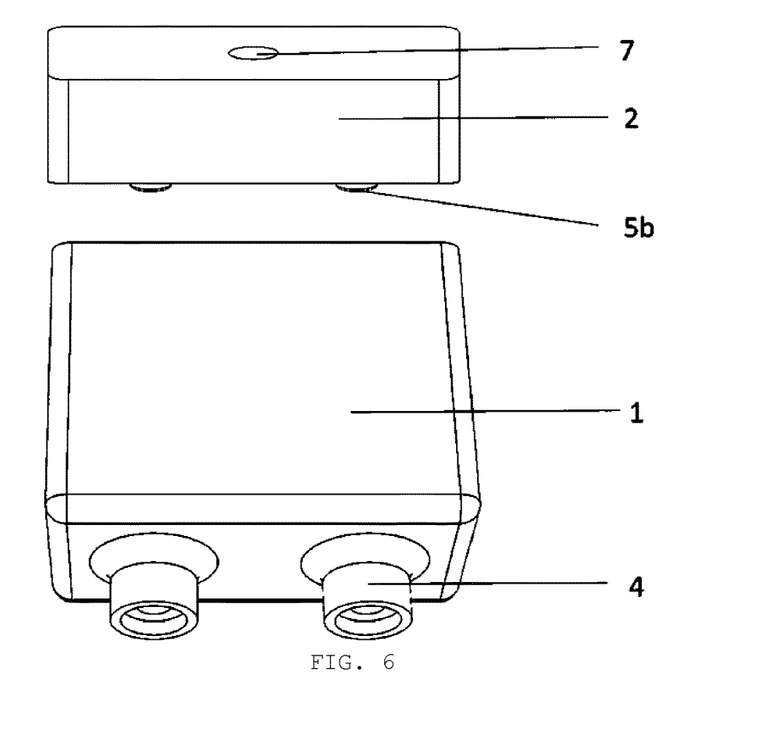
FIG. 6—is another view of a conical male element and a female element, used in an embodiment of the dental prosthesis system.
Figure 7:
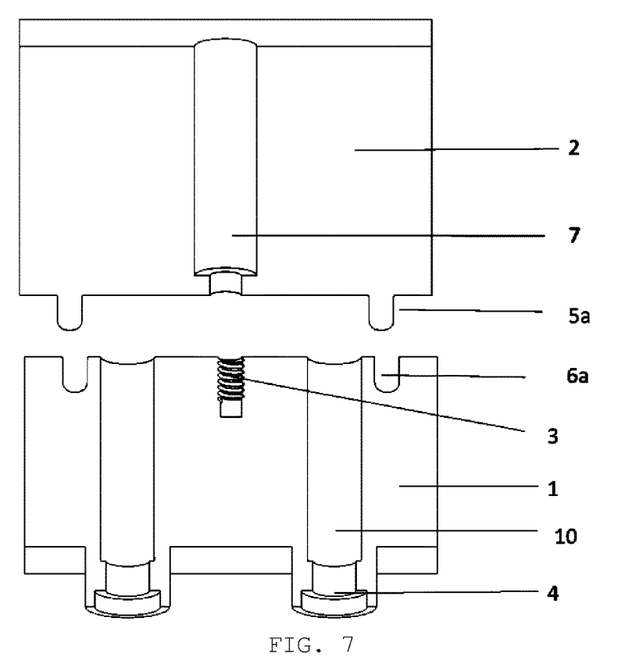
FIG. 7—is a cut view of an embodiment of the dental prosthesis system showing the projection male element and a groove female element, the prosthetic and implant screw channels, used in an embodiment of the dental prosthesis system.
Figure 8:
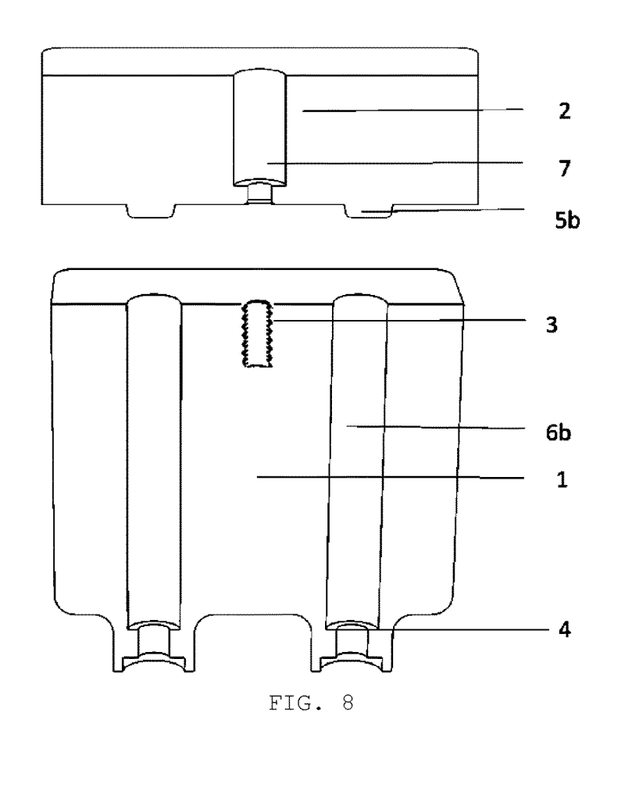
FIG. 8—is a cut view of an embodiment of the dental prosthesis system showing a conical male element and a female element, the prosthetic and implant screw channels, used in an embodiment of the dental prosthesis system.
Figure 9:
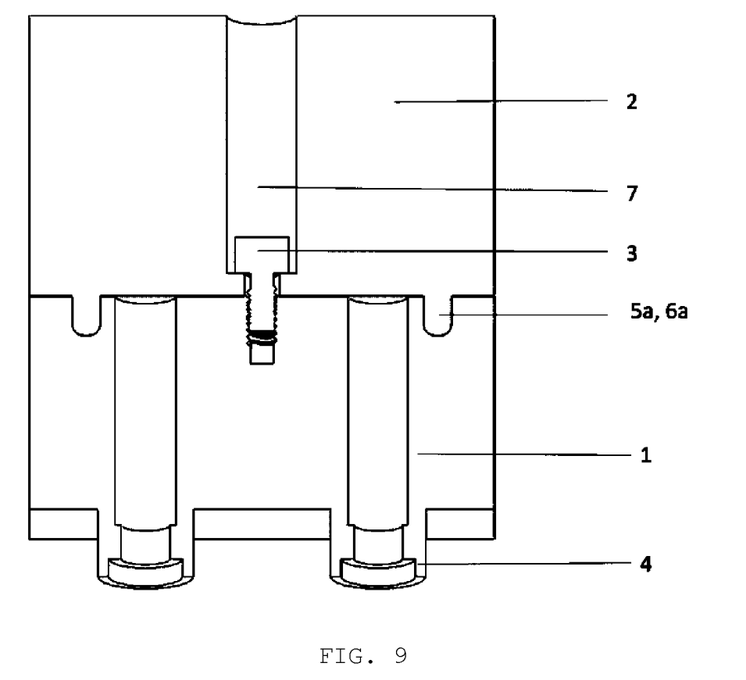
FIG. 9—is a cut view of the assembly of both prosthetic parts showing a projection male element and a groove female element and the prosthetic screw, used in an embodiment of the dental prosthesis system.
Figure 10:
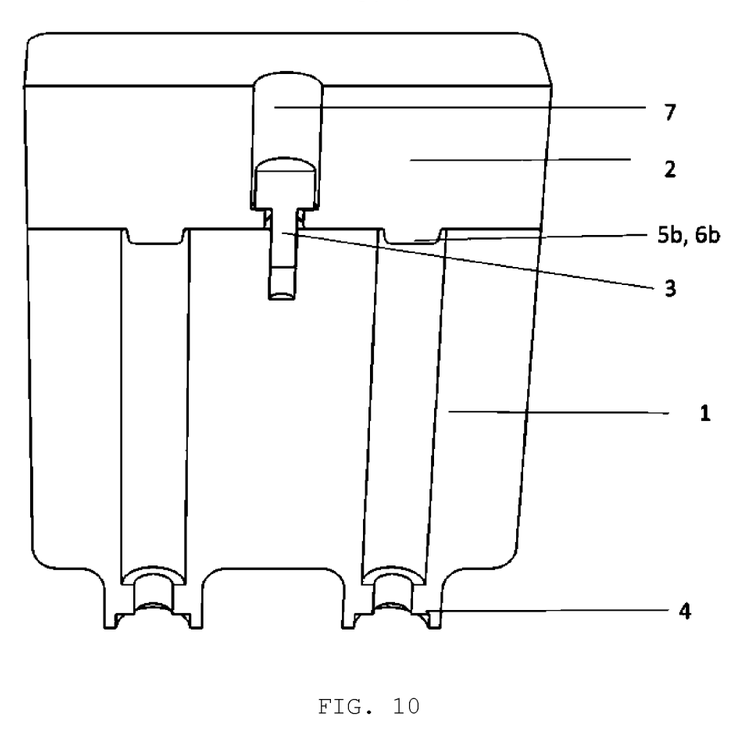
FIG. 10—is another cut view of the assembly of both prosthetic parts showing a conical male element and a female element and the prosthetic screw, used in an embodiment of the dental prosthesis system.

As it is illustrated in FIG. 2, in a more preferred embodiment of the present invention, the division of the dental crown into the first prosthetic part (1) and the second prosthetic part (2) has a slope in a range from 5 degrees to 25 degrees, wherein such slope is related to the horizontal plane formed by the bottom section of the first prosthetic part (1) or the top section of the second prosthetic part (2). Preferably, the division of the first prosthetic part (1) and the second prosthetic part (2) has about 10 degrees slope. This preferred embodiment potentializes the creating of a mechanical weakness in the prosthetic screw (3), that acts protecting the bone tissue from stresses related with woven bone formation.

In the FIGS. 1 and 2, the dental prosthesis system is placed over a model of a cortical bone (8), which comprises in its inner part a model of a trabecular bone (9). The upper section of the cortical bone (8) aims to represent the crestal cortical bone.

In the preferred embodiments of the present invention, wherein the interfaces between the first prosthetic part (1) and the second prosthetic part (2) are tilted, analysing the displacements suffered by the dental prosthesis system, it is possible to confirm that the second prosthetic part (2) slides over the first prosthetic part (1), from lingual face to buccal face. The displacement of the second prosthetic part (2) results in a generation of a shear stress and further fracture or deformation of the prosthetic screw (3). Therefore, tilting the interface between both prosthetic parts increases the possibility of creating a mechanical weakness on the prosthetic screw that could act protecting the bone tissue from stresses related with woven bone formation.

In the preferred embodiments of the present invention, wherein the interfaces between the first prosthetic part (1) and the second prosthetic part (2) are tilted, the height of the second prosthetic part (2) is equal or superior to 5 mm depending on the height of the anatomical crowns that are intended to be replaced, considering its buccal face.

In another preferred embodiment of the present invention, the first prosthetic part (1) has the dimension of a bone and gingiva, that the first prosthetic part (1) intends to replace, and the second prosthetic part (2) has the dimension of the lost teeth, that the second prosthetic part (2) intends to replace.

As it is illustrated in FIGS. 3, 5, 7 and 9, in preferred embodiments of the present invention, the engaging system is composed of two projections as male elements (5a) and two corresponding grooves as female elements (6a), wherein the two projections as male elements (5a) and the two corresponding grooves as female elements (6a) are disposed transversely, respectively along the second prosthetic part (2) bottom section and the first prosthetic part (1) top section. In other embodiments according to the present invention, the two corresponding grooves as female elements (6a) may be deeper than the length of the two projections as male elements (5a). The deeper features of the two corresponding grooves as female elements (6a) contribute to a greater rotation of the second prosthetic part (2) and, therefore, such increased rotation generates higher shear stress on the prosthetic screw (3).

As it is illustrated in FIGS. 4, 6, 8 and 10, in other preferred embodiments of the present invention, the engaging system is composed of two conical or cylindrical extensions as male elements (5b) and two corresponding conical or cylindrical cavities as female elements (6b). In a preferred embodiment, the cavities as female elements (6b) correspond to the channels leading to the connectors (4), wherein such channels are used to introduce and screw the implant screws to implants.

In another preferred embodiment of the present invention, the material of the prosthetic screw (3) may be selected from several materials, for example, a metal, an alloy, a ceramic, a polymer or a reinforced polymer. Preferably, the material of the prosthetic screw (3) is selected from a titanium alloy, for example titanium grade V alloy (Ti6Al4V), a cobalt-chrome alloy, zirconia and polyether ether ketone (PEEK), wherein the polyether ether ketone is optionally reinforced with carbon fibres or glass fibres.

In another preferred embodiment of the present invention, the materials of the first prosthetic part (1) and the second prosthetic part (2) are selected from the group consisting of a metal, an alloy, a ceramic, a polymer or a reinforced polymer. Preferably, the materials of the first prosthetic part (1) and the second prosthetic part (2) are commercial pure titanium, titanium alloys, for example titanium grade V alloy (Ti6Al4V), cobalt-chrome alloys, zirconia, representing the ceramics materials, and polyether ether ketone (PEEK), representing the polymeric materials, wherein the polyether ether ketone is optionally reinforced with carbon fibres or glass fibres.

The implants upon which it is possible to use the dental prosthesis system according to the present invention are all the commonly known in the prior art. Among others, the implants may be selected from endosseous implants, subperiosteal or crestal implants; trans-mandibular implants; blade implants; whether the implant material is commercial pure titanium, titanium alloys, zirconia, titanium-zirconia alloys, aluminium oxide implants or others.

The dental prosthesis system according to the present invention may be connected to the implants or to intermediate abutments by means of implant screws, wherein the materials of the implant screws are selected from the commonly used, for example, a metal and an alloy, usually prepared from an alloy Ti6Al4V ELI. Alternatively, the dental prosthesis system may be connected to the implants using a cemented technique, wherein the materials of the abutments for cementation and the materials of the cement are any of commonly used for the same effect in the previous state of the art.

The present invention also comprises a method of using at least two implants and the dental prosthesis system according to the present invention, which may be employed in a huge field of applications, such as the clinical situations associated with a decrease of the bone volume. Examples of such clinical situations include the teeth lost, which often results in severe bone remodelling, long term use of removable dentures, oncologic diseases related clinical situations, such as marginal mandibulectomies or segmental mandibulectomies followed by mandible reconstructions with different approaches, oral infections, for example periodontal or peri-implant diseases, and trauma, for example mandible fractures resulting from accidents.

The method of using at least two implants and the dental prosthesis system according to the present invention comprises the steps of:
  a) Performing the placement of at least two implants into the bone jaw, whether the option of the surgeon is on a free handed, fully guided or partially guided technique, whether it is an immediate, delayed or late implant placement and whether it is a flap or a flapless procedure;
  b) Placing the dental prosthesis system according to the present invention attached to the implants.

In the method of using at least two implants and the dental prosthesis system according to the present invention, the implant placement step should follow the drilling protocols recommended by the chosen implant manufacturer.

During the process of placing the dental prosthesis system, the first prosthetic part is attached to the implants by two possible manners:
  a) Screwed, using the adequate torque, directly to the implant platform or to intermediate abutments.
  b) Cemented to abutments screwed to the implants for that effect.

Then, the second prosthetic part is attached to the first one, by means of the prosthetic screw, with a precise torque, using a torque-controlled device.

The following examples are for the purpose of illustration only and are not to be construed as limiting the scope of the invention in any way.

The examples 1 to 3 are simulations under a finite element analysis (FEA), which is widely used in dental implantology, to evaluate the biomechanical behaviour of living tissues and restorative materials. The recourse to this method allows the multiplication of tests in a small period of time, varying the critical factors of each experience, in a manner that would be undoable with experimental biomechanics or animal and clinical testing.

The FEA analysis used to evaluate the present invention considered the bone as a transversely isotropic material, according to the methodology known in O'Mahony et al. ("Anisotropic elasticity of cortical and cancellous bone in the posterior mandible increases peri-implant stress and strain under oblique loading". Clin Oral Implan Res. 2001; 12(6):648-57).

In order to bring the mathematical model as close as possible to reality, the model parts were designed based on measurements directly made on computerized tomographys of real patients, product catalogs from implant companies and reverse engineering methods. The interactions between the different parts respected the real situation. For example, to simulate the osteointegration of the dental implants, the three model parts "cortical bone", "trabecular bone" and "dental implants" were merged, in the "assembly" menu of the abaqus software, used in the FEA analysis, retaining the parts boundaries, which made possible the assignment of different materials.

The loading conditions were collected from bibliography to simulate real conditions according to Baca et al. (In vivo evaluation of occlusal contact area and maximum bite force in patients with various types of implant-supported prostheses. Acta Odontol Scand. 2013; 71:1181-7).

A mesh sensitivity analysis was performed, and the mathematical models were experimentally validated.

EXAMPLE 1

The table 1 presents the results related to a comparison of the computed stresses, the microgap and displacements, between a reference model (conventional one-part prosthetic framework) and a tilted plan model of dental prosthesis system (divided prosthetic framework).

The results of table 1 were established to a simulated model according to a present invention, wherein the division of the dental crown into the first prosthetic part (1) and the second prosthetic part (2) had a slope of 10 degrees. In this model, it was used a conical extension as male element (5b) which fit in the implant screw channel placed in the first prosthetic part (6b). The model was specified with two connectors (4), a crown height space of 25 mm and the height of the second prosthetic part (2) was of 7 mm on the buccal side of the dental prosthesis system, in order to simulate an average mandibular molar and pre-molar clinical crown height. In this simulated model were designed M 1.4 prosthetic screws. During the simulation, the following materials were assigned to the parts: to prosthetic screw and implant screw the alloy Ti6Al4V, to prosthetic parts and prosthesis the cobalt-chrome alloy and to implants the commercial pure titanium grade IV.

TABLE 1

(results from example 1)

| Part | Unit | Reference model (before prosthetic division) | Model of present invention | Materials' yield strength |
|---|---|---|---|---|
| Bone | MPa | 60.99 | 51.89 | 60 |
| Implants | | 454.2 | 301.4 | 750 |
| Implant screw | | 214.6 | 181.1 | 795 |
| Prosthetic screw | | Not applicable | 879.6 | 795 |
| Prosthesis | | 183.4 | Not applicable | 659 |
| First prosthetic part | | Not applicable | 171.0 | 659 |
| Second prosthetic part | | Not applicable | 127.8 | 659 |
| Microgap | μm | 5.5 | 4.45 | Not applicable |
| Displacement | | 127 | 117.2 | Not applicable |
| Step time | | 0.6 | 0.5 | Not applicable |

Analyzing the table 1, it is possible to observe that the stress obtained in the implants suffered a decrease from 454.2 MPa on the reference model to 301.4 MPa on the model according to the present invention. Comparing the stresses computed at the implant-abutment connection, considering the prosthesis part for the reference model and the first prosthetic part for the model according to the present invention, and also comparing the stress computed on the implant screws, the present model shows on both parameters a decrease on the stress values. The microgap, which in the numerical simulations represents the distance between the implant platform and the prosthesis connectors, calculated based on the movement of the prosthetic part at the connectors level and not resulted from a poor fit, also shows a smaller value in the model according to the present invention, indicating a micromovement of smaller amplitude than the predicted for the reference model.

These results reflect a new solution, where the biological tissues may be preserved and the prosthetic components show a stress pattern bellow the plastic deformation, wherein the prosthesis is divided in two parts, one representing the teeth and the other one representing the lost bone, wherein its assembly is performed by means of a prosthetic screw, that acts as a shear screw.

EXAMPLE 2

It is possible to increase the shear stress in the prosthetic screw with even higher magnitudes, allowing its fracture, before the bone has reached a stress state compatible with a bone remodeling. When the stress applied to the bone is superior to 60 MPa, microdamages can begin to accumulate unrepaired and the woven bone formation begins to replace the lamellar bone formation. In order to potentialize the action of the prosthetic screw as a sacrificial element, it is necessary to expose the prosthetic screw to the effect of a horizontal component of the applied load. This force component is the one responsible for the rotation of the second part prosthetic part, which is greater than the rotation of the first prosthetic part, resulting in bending and shear solicitations and a pull-out movement of the prosthetic screw.

The results of table 2 were established to a simulated model according to a present invention, wherein it was used a projection as male element (5a) and a groove as female element (6a), wherein the groove was deeper than the projection length. The model was specified with two connectors (4), a crown height space of 25 mm and the height of the second prosthetic part (2) was of 6 mm, in order to simulate an average mandibular molar and pre-molar clinical crown height. In this model were designed M 1.4 prosthetic screws. During the simulation, the following materials were assigned to the parts: to implant screw the alloy Ti6Al4V, to prosthetic parts the cobalt-chrome alloy, to implants the commercial pure titanium grade IV and to prosthetic screw the unfilled PEEK.

TABLE 2

(results from example 2)

| Part | Unit | Model of present invention | Materials' yield strength |
|---|---|---|---|
| Bone | MPa | 57.84 | 60 |
| Implants | | 204.1 | 750 |
| Implant screw | | 211.1 | 795 |
| Prosthetic screw | | 98.37 | 98 |
| First prosthetic part | | 192.0 | 659 |
| Second prosthetic part | | 117.0 | 659 |
| Microgap | μm | 4.57 | Not applicable |
| Displacement | | 139.2 | Not applicable |
| Step time | | 0.6 | Not applicable |

EXAMPLE 3

Another possible approach to increase the effects of the horizontal component of the applied load over the prosthetic screw is to increase the height of the second prosthetic part (2) in relation to the first prosthetic part (1). This would result in a torque increase and, therefore, in a higher shear stress at the prosthetic screw level.

The results of table 3 were established to a simulated model according to a present invention, wherein the height of the second prosthetic part (2) was at half of the existent crown height space. In this model, it was used a projection as male element (5a) and a groove as female element (6a), wherein the groove had the same length than the projection. The model was specified with two connectors (4) and a crown height space of 25 mm. In this model were used conventional M 1.4 prosthetic screws. During the simulation, the following materials were assigned to the parts: to implant screw the alloy Ti6Al4V, to prosthetic parts the cobalt-chrome alloy, to implants the commercial pure titanium grade IV and to prosthetic screw the unfilled PEEK.

TABLE 3

(results from example 3)

| Part | Unit | Model of present invention | Materials' yield strength |
| --- | --- | --- | --- |
| Bone | MPa | 34.49 | 60 |
| Implants | | 149.4 | 750 |
| Implant screw | | 154.8 | 795 |
| Prosthetic screw | | 103.2 | 98 |
| First prosthetic part | | 161.8 | 659 |
| Second prosthetic part | | 53.82 | 659 |
| Microgap | μm | 8.9 | Not applicable |
| Displacement | | 136.2 | Not applicable |
| Step time | | 0.3704 | Not applicable |

As it shown in Tables 2 and 3, the computed results from the finite elements analysis place the bone tissue in a safe stress zone while the prosthetic screw overcomes the elastic limit.

Due to all the approximations, assumptions and simplifications during the finite element analysis, the numerical model was experimentally validated. For this purpose, an experimental model was designed and manufactured. The choice of a 30 degrees slope loading model, also used in the numerical simulation, intended to equate the physiological forces resulting from mastication and was determined because such slope corresponds to a worst-case scenario. Besides, such slope is specified in the ISO standard 14801, which rules the fatigue tests on dental implants.

The model manufactured according to a present invention to validate the simulations performed comprised a height of the second prosthetic part (2) established as half of the existent crown height space. In this manufactured model, it was used a projection as male element (5a) and a groove as female element (6a), wherein the groove had the same length than the projection. The model was specified with two connectors (4) and a crown height space of 25 mm. In this model were used conventional M 1.4 prosthetic screws. During the manufacturing of this model, the prosthetic parts were prepared from a cobalt-chrome alloy, the implant screw was prepared from the alloy Ti6Al4V, and the prosthetic screw was prepared from unfilled PEEK. For economic reasons, implants dummies were used once the alloy of which they are made up, Ti6Al4V alloy, has elastic properties in the same range of the commercial pure titanium grade IV. The resin that substitutes the bone part was an epoxy meeting the standards of ISO 14801.

After establishing the final set up geometry, four samples were submitted to a quasi-static load compressive test. The test was interrupted when the applied load magnitude record showed a sharp decrease.

During the test, it was verified that the second prosthetic part rotates and slides over the first one creating an opened joint on the lingual side. As a result, it was possible to observe that unfilled PEEK prosthetic screw of the samples 1 and 2 suffered a necking process characterized by the diameter reduction and elongation of the screw's body and in the samples 3 and 4 the experiment ended with the screw fracture. In all the samples, the resin that replaces the bone, the implants, the implant screws and both prosthetic parts remained without damage.

The described experimental behavior exhibited by the samples is like that shown by the finite element analysis. The second prosthetic part suffers a sliding movement and a rotation of bigger dimension than the first part which creates a lingual opened joint. That phenomenon generates shear and bending stresses in the prosthetic screw, that exceed the material elastic limit, resulting in the screw deformation (necking) or fracture. For the same load, the other components of the model do show stresses under the yield strength of the correspondent materials.

Figure 11:
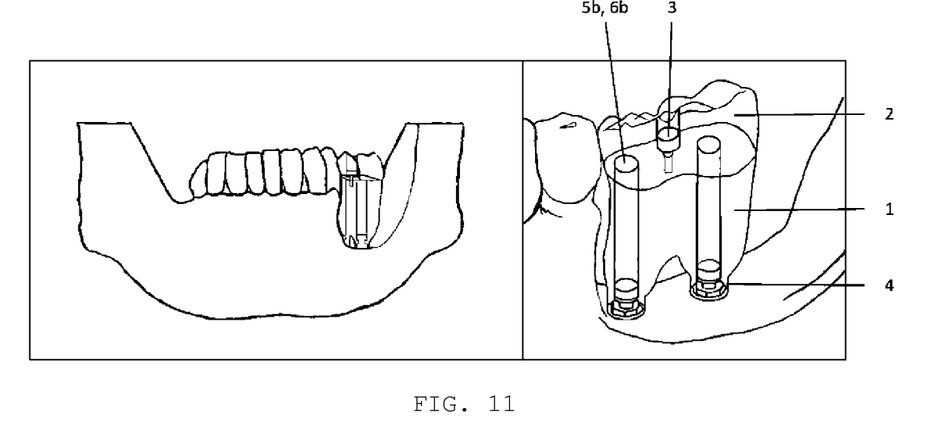
FIG. 11—is a view of a dental prosthesis system after incorporating anatomical bone and teeth features.

Nonetheless, it will be understood by those skilled in the art that in other alternative embodiments the prosthetic parts of the dental prosthesis system according to the present invention may be manufactured after including teeth and bone anatomic features, such as geometries of teeth, as it is shown on FIG. 11. In the embodiment represented on FIG. 11, a tilted plan model was incorporated in a dental prosthesis system according to the present invention, considering anatomical bone and teeth features.

Moreover, the dental prosthesis system according to the present invention is suitable for connection to both external connection implants and internal connection implants, for example the Morse tapered internal connections with the integration of the platform shifting concept.

The dental prosthesis system according to the present invention is also suitable for connection to intermediate abutments, for example straight or angled multi-unit type.

The first prosthetic part of the dental prosthesis system according to the present invention is also suitable for connection to the implants by means of a cemented approach.

The first prosthetic part of the dental prosthesis system according to the present invention may also incorporate the angulated screw channel concept.

As used herein, the term "longitudinal" refers to a plane of cut of a device or component comprised on the largest dimension in said device. On the other hand, the term "transverse" refers to the plane of cut of a device or component comprised on the smallest dimension in said device.

The terms "about" and "approximately" are understood to refer to a range of values of plus or minus 10% of the number specified.

The term "substantially" is understood to refer a condition that the actual value is within the range of about 10% of the desired value, variable or related limit, particularly within about 5% of the desired value, variable or related limit or especially within about 1% of the desired value, variable or related limit.

The subject matter described above is provided as an illustration of the present invention and should not be construed as limiting it. The terminology employed for the purpose of describing specific embodiments in accordance with the present invention should not be construed to limit the invention. As used in the description, definite and indefinite articles, in their singular form, aim at the interpretation of including also the plural forms, unless the context of the description explicitly indicates the contrary. It will be understood that the terms "comprise" and "include", when used in this disclosure, specify the presence of features, elements, components, steps and related operations but do not exclude the possibility of other features, stages and operations are also contemplated.

All changes, if they do not modify the essential features of the claims which follow, are to be considered within the scope of the protection of the present invention.

The invention claimed is:

1. A dental prosthesis system with a mechanical weakness, for the use with at least two dental implants, comprising:
   a first prosthetic part, with a mesial, distal, lingual and buccal faces, a top section and a bottom section;
   a second prosthetic part, with a mesial, distal, lingual and buccal faces, a top section and a bottom section;
   a sacrificial prosthetic screw, joining the first prosthetic part and the second prosthetic part, and configured to deform or fracture in the event of excess load due to mastication force or fatigue use;
   at least two screw channels leading to at least two connectors arranged in the bottom section of the first prosthetic part, wherein the at least two screw channels are configured to introduce implant screws; and
   an engaging and guiding system comprising two female elements disposed on the top section of the first prosthetic part, and two corresponding male elements disposed on the bottom section of the second prosthetic part, wherein the two female elements and the two corresponding male elements are releasably connected, wherein the first prosthetic part is connected to at least two dental implants through the at least two connectors,
   wherein the mechanical weakness is provided by the sacrificial prosthetic screw.

2. The dental prosthesis system, for the use with at least two dental implants, according to claim 1, wherein the first prosthetic part and the second prosthetic part are divided horizontally, and wherein a height of the second prosthetic part corresponds to the vertical dimension of the dental crown of a patient, having a value of between 6 and 10 mm, which corresponds to a range from 20% to 80% of an existing crown height space.

3. The dental prosthesis system, for the use with at least two dental implants, according to claim 1, wherein the first prosthetic part and the second prosthetic part has a slope in a range from 5 degrees to 25 degrees, wherein the slope is related to an horizontal plane formed by the bottom section of the first prosthetic part or the top section of the second prosthetic part.

4. The dental prosthesis system, for the use with at least two dental implants, according to claim 3, wherein a height of the second prosthetic part is equal or superior to 5 mm on a side wherein the second prosthetic part is highest along a longitudinal plane of an existing crown height space.

5. The dental prosthesis system, for the use with at least two dental implants, according to claim 2, wherein the crown height space is equal or superior to 15 mm.

6. The dental prosthesis system, for the use with at least two dental implants, according to claim 1, wherein the second prosthetic part has a vertical dimension of a lost tooth and the first prosthetic part occupies a remaining space between the implant platform and a bottom of the second prosthetic part, and wherein the first prosthetic part has a dimension of a bone and gingiva, that the first prosthetic part intends to replace, and the second prosthetic part has a dimension of lost teeth, that the second prosthetic part intends to replace.

7. The dental prosthesis system, for the use with at least two dental implants, according to claim 1, wherein the two corresponding male elements comprise two projections and the two female elements comprise two grooves, wherein the two corresponding male elements comprising two projections and the two corresponding female elements comprising two grooves are disposed transversely, from palatal/lingual to buccal, respectively along the second prosthetic part bottom section and the first prosthetic part top section.

8. The dental prosthesis system, for the use with at least two dental implants, according to claim 7, wherein the two female elements comprising two grooves are deeper and longer than the two corresponding male elements comprising two projections.

9. The dental prosthesis system, for the use with at least two dental implants, according to claim 1, wherein the corresponding male elements comprises two conical or cylindrical extensions and the two female elements comprises two conical or cylindrical cavities.

10. The dental prosthesis system, for the use with at least two dental implants, according to claim 9, wherein the two female elements comprising two conical or cylindrical cavities correspond to the at least two screw channels leading to the at least two connectors.

11. The dental prosthesis system, for the use with at least two dental implants, according to claim 1, wherein the prosthetic screw is made from a material selected from the group consisting of a metal, an alloy, a ceramic, a polymer and a reinforced polymer.

12. The dental prosthesis system, for the use with at least two dental implants, according to claim 11, wherein the material of the prosthetic screw is selected from a titanium alloy, a cobalt-chrome alloy, zirconia and polyether ether ketone, wherein the polyether ether ketone is optionally reinforced.

13. The dental prosthesis system, for the use with at least two dental implants, according to claim 1, wherein the first prosthetic part and the second prosthetic part are made from a material selected from the group consisting of a metal, an alloy, a polymer, a reinforced polymer and a ceramic.

14. The dental prosthesis system, for the use with at least two dental implants, according to claim 13, wherein the materials of the first prosthetic part and the second prosthetic part are selected from the group consisting of titanium alloys, cobalt-chrome alloys, titanium, zirconia, ceramics materials, and polyether ether ketone (PEEK), wherein the polyether ether ketone is optionally reinforced with carbon fibre or glass fibre.

15. The dental prosthesis system, for the use with at least two dental implants, according to claim 12, wherein the titanium alloy is titanium grade V alloy (Ti6Al4V).

16. The dental prosthesis system, for the use with at least two dental implants, according to claim 14, wherein the titanium alloy is titanium grade V alloy (Ti6Al4V).

* * * * *